United States Patent [19]
Haddad

[11] Patent Number: 6,103,935
[45] Date of Patent: Aug. 15, 2000

[54] PROCESS FOR PRODUCTION OF FUMARIC ACID BY ISOMERIZATION OF MALEIC ACID

[75] Inventor: Muin S. Haddad, Naperville, Ill.

[73] Assignee: BP Amoco Corporation, Chicago, Ill.

[21] Appl. No.: 09/295,955

[22] Filed: Apr. 21, 1999

[51] Int. Cl.$^7$ .............................. C07C 51/00; C07C 57/15
[52] U.S. Cl. ............................................. 562/591; 560/595
[58] Field of Search ...................................... 562/591, 595

[56] References Cited

U.S. PATENT DOCUMENTS 2,393,352  1/1946  Winstrom .
2,816,922  12/1957  Stephenson .
2,816,923  12/1957  Stephenson .

FOREIGN PATENT DOCUMENTS 250260  9/1986  Czechoslovakia .
273818  of 1973  U.S.S.R. .

*Primary Examiner*—Gary Geist
*Assistant Examiner*—Leigh C. Maier
*Attorney, Agent, or Firm*—Mary Jo Kanady; Wallace L. Oliver

[57] ABSTRACT

The present invention relates to a process for the production of fumaric acid by the isomerization of maleic acid at high conversions which comprises heating maleic acid in the presence of phosphoric acid at a temperature sufficient to isomerize the maleic acid to fumaric acid.

23 Claims, No Drawings ic acid, calculated from maleic anhydride and water, and up to 20 wt % hydrochloric acid, 33–37% relative to the amount of maleic anhydride used, is heated to boiling at pressure of 0.2–2 MPa for a time of 0.25–8 hours, followed by isolation of the fumaric acid from the reaction mixture.

PROCESS FOR PRODUCTION OF FUMARIC ACID BY ISOMERIZATION OF MALEIC ACID

BACKGROUND OF THE INVENTION

The present invention relates to a process for the production of fumaric acid by the isomerization of maleic acid at high conversions which comprises heating maleic acid in the presence of phosphoric acid at a temperature sufficient to isomerize the maleic acid to fumaric acid. The process provides high purity fumaric acid in good yields.

Fumaric acid us used in the manufacture of paper sizing resins; as a food additive, especially as a food acidulant in products such as fruit juices, gelatin desserts, and animal feed; in unsaturated polyester resins; in alkyd coatings; in the manufacture of inks, and in other applications. Purity of the fumaric acid is particularly important when it is used as a food additive.

Fumaric acid has been traditionally produced by isomerization of maleic acid in water in the presence of catalysts such as bromine, bromide, sulfuric acid, hydrochloric acid and thiosulfites. A disadvantage of these processes is that the agents used as catalysts and co-catalysts have adverse effects on the environment, cause serious disposal problems, and require further purification of the fumaric acid to convert it into a product with acceptable, odor, color, and quality. These all add significantly to the costs of producing fumaric acid, particularly fumaric acid of food grade quality, which is the quality usually preferred.

SU273818 discloses a method of producing fumaric acid by using a strong acid and one or more catalysts, such as ammonium bromide, ammonium persulfate, ammonium bromide, ammonium persulfate, or thiourea to isomerize aqueous solutions of maleic acid. The strong acids, for example, sulfuric, hydrochloric, orthophosphoric, oxalic and other acids that are as strong as maleic acid are introduced into the maleic acid solution along with the catalyst prior to isomerization. The isomerization is conducted at 65–80° C., optimally at 70–72° C.

CS 250 620 B1 discloses a process for producing fumaric acid in the presence of hydrochloric acid as the catalyst wherein the reaction mixture formed of maleic acid and hydrochloric acid with a concentration of 50–90 wt % maleic acid, calculated from maleic anhydride and water, and up to 20 wt % hydrochloric acid, 33–37% relative to the amount of maleic anhydride used, is heated to boiling at pressure of 0.2–2 MPa for a time of 0.25–8 hours, followed by isolation of the fumaric acid from the reaction mixture.

U.S. Pat. No. 2,393,352 discloses a process of manufacturing fumaric acid from maleic anhydride-containing converter gases by absorbing the maleic anhydride vapors in aqueous mineral acid solutions, such as hydrochloric acid, hydrobromic, acid hydroiodic acid, and sulfuric acid. Nitric acid is disclosed to be useable but less desirable due to its oxidizing tendencies. The maleic anhydride gases are cooled to 40° C. to 60° C. (but not below the dew-point of the gaseous mixtures with respect to maleic anhydride) so as to avoid raising the temperature of the hydrochloric acid solution to its boiling point. The resulting hydrochloric acid solution may be heated to 80° C. to 100° C. in order to complete the conversion of the maleic acid present to fumaric (in admixture with the precipitated fumaric acid or after removal of the precipitate). However, it is noted that unless equipment is provided for the recovery of mineral acid and its maintenance in the Absorber (e.g., by the use of superatmospheric pressure) certain of the beneficial advantages of the preferred process will not be obtained, such as efficient reuse of the mineral acid.

U.S. Pat. No. 2,816,922 discloses a process for the production of fumaric acid from aqueous maleic acid liquors, particularly those resulting from the production of phthalic anhydride, involving the steps of heating in a conversion zone a concentrated maleic acid liquor, that is, one from which a major proportion of the water has been removed, to vaporize additional water and to convert the maleic acid into fumaric acid. In a more specific embodiment, the process for noncatalytically converting maleic acid contained in relatively dilute aqueous maleic acid solutions containing up to about 30% by weight of maleic acid to fumaric acid, comprises heating the dilute maleic acid to an elevated temperature below about 250° F. in a concentration zone to evaporate water from the dilute solution and produce a concentrated maleic acid solution containing about 70–90% by weight of maleic acid, heating the concentrated maleic acid by raising the temperature of the liquor, preferably by submerged combustion, to a temperature above 250° F. and below about 400° F. in a conversion zone to produce a slurry of fumaric acid in aqueous maleic acid, withdrawing a vapor stream comprising steam and maleic anhydride from the conversion zone and passing it into the concentration zone, withdrawing said slurry from the conversion zone, diluting the withdrawn slurry with concentrated maleic acid solution, separating the diluted slurry into a liquid phase comprising aqueous maleic acid and a solid phase comprising crude fumaric acid and returning the liquid phase to the conversion zone. A disadvantage of this process is that the crude fumaric acid contains impurities, such as phthalic acid, and must be further treated to purify it. The purification treatment requires subjecting the crude fumaric acid to a decolorization process using, e.g., carbon, then separating the carbon, recrystallizing the fumaric acid, and drying it.

U.S. Pat. No. 2,816,923 discloses a process for the production of fumaric acid from aqueous maleic acid liquors, particularly those resulting from the production of phthalic anhydride, involving the steps of heating in a reaction zone a maleic acid liquor to form a top vapor phase of maleic anhydride, and a bottom fraction of fumaric acid crystals in a maleic anhydride melt. The top vapor phase and water pass into an adsorption zone wherein the maleic anhydride is absorbed and the water is allowed to escape from the system. The bottom fraction is joined with fresh maleic acid feed as it issues from the reaction zone, and the resulting aqueous stream is introduced into a separation zone, wherein the crude fumaric acid crystals are separated and the liquid passed into the adsorption zone wherein the maleic anhydride is scrubbed from the vapors or absorbed by the liquid, the resulting mixture then going into the reaction zone. A disadvantage of this process is that the separated crude fumaric acid crystals contain impurities, such as phthalic acid, and must be purified in additional process steps. The purification treatment involves decolorization, recrystallization, and drying.

Applicant has made the surprising and unexpected discovery that maleic acid can be isomerized at high conversions to give fumaric acid of excellent color and quality by heating the maleic acid in the presence of phosphoric acid under conditions suitable to cause isomerization of the maleic acid to fumaric acid. The fumaric acid product can be recovered by filtration or other means. Such a process conveniently makes a fumaric acid product in a yield of at least about 30 wt %, preferably at least about 50 wt % yield, more preferably at least about 60 to about 80 wt % yield, even more preferably at least about 90 wt %, still more preferably at least about 95 wt %, yet more preferably, at least about 98 wt %, and most preferably at least about 100 wt %. The fumaric acid product can optionally be further purified by washing with water. It is unexpected that the isomerization of maleic acid to fumaric acid can be conducted using phosphoric acid without the addition of catalysts.

The present invention advantageously provides a process for making very high purity fumaric acid by isomerizing maleic acid at high conversions to give fumaric acid of good quality and color without the need to add undesirable catalysts. The fumaric acid is easily recovered by filtration or other means, and a simple water wash almost completely removes any remaining phosphoric acid so that the fumaric acid product is readily purified.

The mother liquor is completely recyclable for use in consecutive reaction batches. Because the only components used in the reaction mixture are maleic anhydride and/or maleic acid, phosphoric acid, and water, it is believed that the process of the present invention will meet the stringent requirements for producing food grade fumaric acid, and that the process is more environmentally acceptable than known processes for making fumaric acid.

The exclusive use of phosphoric acid in the present invention has the advantages of permitting the complete recycling of the mother liquor from the reaction, and mitigating the environmental hazards associated with catalysts, such as bromine, thiourea and its derivatives, thiosulfate, potassium thiocyanate, colloidal sulfur, hydrogen sulfide and sulfuric acid together, hydrohalic acids, ammonium bromide, ammonium persulfate, thiourea etc. which have previously been used for isomerizing maleic acid to fumaric acid. Use of chloride containing compounds, such as hydrochloric acid, as catalysts for the reaction may cause corrosion of the reactor metal as may the use of harsh oxidizing acids such as hydrobromic acid, hydroiodic acid, sulfuric acid and nitric acid. With chloride-containing acids such as hydrochloric acid, there may also be a possibility of formation of chlorinated hydrocarbon by-products which is undesirable.

The fact that in the present invention the mother liquor can be recycled also has the advantage of reducing costs. Since chlorinated hydrocarbon byproducts and other undesirable by-products are not formed in the process of the present invention, the mother liquor from the reaction can be recycled and used to prepare additional fumaric acid. This provides a cost advantage since phosphoric acid supply costs and disposal costs are greatly reduced.

Another advantage of the process of the present invention is that the process can be conducted at high temperatures without the use of pressure equipment such as an autoclave. This reduces costs since it avoids the need to purchase equipment for conducting the process under pressure and also provides for a more convenient process. The high temperatures and pressures required in other processes require the use of cumbersome and expensive production installations such as high-pressure autoclaves.

SUMMARY OF THE INVENTION

The present invention relates to a process for the production of fumaric acid which comprises heating maleic acid in phosphoric acid at a temperature sufficient to isomerize said maleic acid to produce fumaric acid.

The invention further relates to a process for producing fumaric acid comprising: heating maleic acid and an aqueous solution of phosphoric acid to reflux to isomerize the maleic acid to fumaric acid and then removal of the aqueous phosphoric acid solution from the fumaric acid precipitate formed to recover the fumaric acid product. Optionally, the fumaric acid product may be further purified by washing it with water.

In the process the present invention, the phosphoric acid may optionally be recovered after removal of the fumaric acid product and used to isomerize a fresh batch of maleic acid. The ability to recover and reuse the phosphoric acid provides additional cost savings.

The process of the present invention is conducted in the absence of catalysts such as bromine, bromides, ammonium bromide, or other bromine compounds, sulfur containing compounds, such as thiosulfites, thiourea and its derivatives, thiosulfate, potassium thiocyanate, colloidal sulfur, hydrogen sulfide and sulfuric acid together, hydrohalic acids, ammonium persulfate, etc. which have previously been used for isomerizing maleic acid to fumaric acid.

The present invention relates to a process for the production of fumaric acid which comprises heating maleic acid in the presence of phosphoric acid at a temperature of from about 212° F. to about 360° F. (about 100° C. to about 182.2° C.) preferably from about 240° F. to about 350° F. (about 115.6° C. to about 176.6° C.); more preferably from about 290° F. to about 340° F. (about 143.3° C. to about 171.1° C.), and most preferably from about 310° F. to about 330° F. (about 154.4° C. to about 165.7° C.) to isomerize the maleic acid to fumaric acid. The reaction mixture may optionally contain water in addition to the maleic acid and phosphoric acid.

The present invention provides a process for converting maleic acid to fumaric acid by heating an aqueous solution of the maleic acid in the presence of phosphoric acid. The use of phosphoric acid in the reaction mixture permits the temperature to be raised to a temperature sufficient to convert maleic acid to fumaric acid without the use of catalysts or pressure apparatus. Because of this, the process can be conducted in an open system at atmospheric pressure. When maleic acid, phosphoric acid, and water are used, the reaction mixture can be refluxed in an open system at atmospheric pressure. The temperature can be controlled by adjusting the amount of water in the reaction mixture or, if no water is used, by adjusting the heat input.

In the process of the invention the maleic acid is heated in the presence of phosphoric acid until the isomerization to fumaric acid is completed. Generally, the reaction mixture is heated for about 0.5 to about 15 hours, preferably for about 1 to about 10 hours, more preferably about 1 to about 5 hours, and still more preferably about 2 to about 4 hours.

When the isomerization reaction is completed, the fumaric acid produced by the process is recovered and, optionally, purified further by washing with water or another suitable solvent. The fumaric acid produced in the process of the present invention may be recovered by any suitable means, including filtration, centrifugation and the like. The phosphoric acid-containing mother liquor may be reused to isomerize a fresh batch of maleic acid.

In one embodiment of the invention, maleic acid may be obtained from a plant stream of maleic acid solution, such as, for example, that produced as a by-product in the manufacture of maleic anhydride when maleic anhydride vapor is contacted with water in a scrubber.

In another embodiment of the present invention, maleic anhydride can be used as the starting material and hydrolyzed to give maleic acid which is then isomerized in the presence of phosphoric acid to give fumaric acid.

DESCRIPTION OF THE PREFERRED EMBODIMENT(S)

The present invention relates to a process for making fumaric acid of very high purity by isomerization of maleic acid in the presence of phosphoric acid and, optionally, water. Preferably, the fumaric acid product will have a purity of at least about 95%, more preferably about 97% to about 98% purity, and most preferably about 99% to about 100% purity.

In the present invention, maleic acid is heated in phosphoric acid and, optionally, water at a temperature of from about 212° F. to about 360° F. (about 100° C. to about 182.2° C.) preferably from about 240° F. to about 350° F. (about 115.6° C. to about 176.6° C.); more preferably from about 290° F. to about 340° F. (about 143.3° C. to about 171.1° C.), and most preferably from about 310° F. to about 330° F. (about 154.4° C. to about 165.7° C.) to isomerize the maleic acid to fumaric acid.

The concentrations of maleic acid, phosphoric acid, and, optionally, water used in the process of the present invention are selected to provide a reaction mixture which can be heated to a temperature sufficient to isomerize maleic acid to fumaric acid without the use of pressure. This will preferably be a temperature in the range of from about 212° F. to about 360° F. (about 100° C. to about 182.2° C.). The less water in the reaction mixture, the higher the temperature that may be achieved.

Preferably the mole ratio of phosphoric acid to maleic acid will be from about 0.1:1 to about 200:1, more preferably it will be from about 0.5:1 to about 24:1, and most preferably from about 1:1 to about 6:1.

Typically the water to maleic acid mole ratio will range from about 0.1:1 to about 1200:1, more preferably it will be from about 0.5:1 to about 16:1, and most preferably from about 1:1 to about 4:1.

Although maleic acid can be heated in 100% phosphoric acid and converted to fumaric acid without the addition of water, it is desirable to have sufficient water in the reaction mixture to enable the mixture to be refluxed upon heating to a sufficient temperature.

If desired, the initial reaction mixture may contain a dilute aqueous solution of maleic acid and during the course of the reaction, water can be stripped off to increase the weight percent of maleic in solution. By removing water from the reaction mixture in this manner, it is possible to manipulate the boiling point of the reaction mixture and control the temperature at which reflux is achieved. For example, one might start with 5% maleic acid concentration in water and strip water until the maleic acid concentration reaches 90 wt %.

The feeds to the process described herein are maleic acid and phosphoric acid. The phosphoric acid starting material may be obtained from any conventional sources. Typical sources for the phosphoric acid starting material can be a commercially available phosphoric acid such as 85% phosphoric acid (85 wt % phosphoric acid in water) or 105% polyphosphoric acid. A 100% phosphoric acid derived from 105% polyphosphoric acid by the addition of water may also be used.

The maleic acid starting material may be obtained from any conventional source. One can start with solid maleic acid or with a maleic acid solution such as, for example, that obtained by dissolving maleic acid in water or by hydrolyzing maleic anhydride with water. The maleic acid may also be derived from contacting maleic anhydride vapor with water as occurs in a scrubber in the commercial production of maleic anhydride. In general, the mole ratio of maleic acid to phosphoric acid will be in a range of from about 0.1:1 to about 3.3:1.

The present invention relates to a process for the production of fumaric acid which comprises heating maleic acid in the presence of phosphoric acid at a temperature of from about 212° F. to about 360° F. (about 100° C. to about 182.2° C.) preferably from about 240° F. to about 350° F. (about 115.6° C. to about 176.6° C.); more preferably from about 290° F. to about 340° F. (about 143.3° C. to about 171.1° C.), and most preferably from about 310° F. to about 330° F. (about 154.4° C. to about 165.7° C.) for about 1 to about 5 hours, preferably for about 2 to about 4 hours, to isomerize the maleic acid to fumaric acid.

In a preferred embodiment, an aqueous solution or slurry of maleic acid and water containing about 5 weight percent to about 95 weight percent of maleic acid is heated in the presence of phosphoric acid to isomerize the maleic acid and convert it to fumaric acid.

The phosphoric acid used in the process of the present invention is preferably an aqueous solution of orthophosphoric acid and is most preferably an 85 weight % solution of $H_3PO_4$ in water.

In the process of the present invention the amount of phosphoric acid as a percent of the maleic acid used is generally from about 8.0 wt % to about 17,000 wt %, preferably from about 40 wt % to about 2100 wt %, and most preferably about 80 wt % to 510 wt %. The amount of water as a percent of the maleic acid used is from about 1.0 wt % to about 2000 wt %, preferably from about 7 wt % to about 250 wt %, and most preferably from about 15 wt % to about 65 wt %.

The amount of phosphoric acid used is an amount effective to achieve a reaction temperature sufficient to isomerize maleic acid to fumaric acid.

The following examples will serve to illustrate certain embodiments of the invention disclosed herein. These examples should not, however, be construed as limiting the scope of the novel invention as there are many variations which may be made thereon without departing from the spirit of the disclosed invention, as those of skill in the art will recognize.

EXAMPLE 1

A 2-liter round-bottom flask was fitted with a heating mantle, condenser, thermocouple, and stirrer paddle with a glass shaft. To this flask the following ingredients were added: 300 g. (2.58 moles) of maleic acid, 600 g. (33.3 moles) of distilled and deionized water and 100 g. (1.02 moles) of 100% ortho-phosphoric acid. The 100% ortho-phosphoric acid was prepared by hydrolysis of 94 g. of Albright & Wilson's 105% polyphosphoric acid with 6 g. of water at 200° F. (93.3° C.) for 1 hour. Thus the maleic acid concentration was about 33 wt %, the phosphoric acid to maleic acid weight ratio was about 0.33, and the phosphoric acid/maleic acid molar ratio was about 0.39. After applying heat, the reaction mixture achieved a reflux temperature of 219° F. (103.9° C.). The reaction was continued for a total of 11 hours. Upon cooling the clear solution, a white precipitate formed.

This precipitate was separated by filtration, washed and dried in a vacuum oven at 200° F. (93.3° C.) for 16 hours. Infrared spectrum of this solid showed it to be pure fumaric acid. The fumaric acid yield was about 30%.

In all the following Examples, the precipitated fumaric acid was filtered, washed with water and dried as described above.

EXAMPLE 2

In this Example, 100 g. (0.86 mole) of maleic acid, 81 g. of water and 240 g. of 105% polyphosphoric acid [240 g polyphosphoric acid plus 15 g. water which is equal to 255 g.(2.60 moles) of 100% $H_3PO_4$] were added to a round-bottom flask as described in Example 1. It was assumed that 15 g. of the water used was needed for hydrolyzing the polyphosphoric acid to 100% orthophosphoric acid. Thus the remaining water and the maleic acid used constituted a 60 wt % maleic acid solution and the phosphoric acid to maleic acid ratio weight ratio was 2.55 and the phosphoric acid/maleic acid molar ratio was 3.02.

Upon heating, the above reaction mixture achieved a reflux temperature of 290° F. (143.3° C.). Contrary to Example 1 where the hot solution remained clear until it was cooled, white solid precipitation was observed at reflux 35 minutes after start of reflux. The reaction was carried out for a total of 5 hours. The reaction mixture was cooled and filtered. The recovered fumaric acid was washed with water and dried in a vacuum oven at 200° F. (93.3° C.) for 16 hours. The fumaric acid yield was about 55 wt %. Infrared spectroscopy of the product indicated that it was pure fumaric acid. No other components were detected.

EXAMPLE 3

In this Example, 100 g. of maleic acid (0.86 mole), 86 g. of water and 344 g. of 105% polyphosphoric acid were added to a round-bottom flask as described in Example 1, and 21 g. of the water used were assumed to be needed for hydrolyzing the polyphosphoric acid to 100% orthophosphoric acid. Therefore, 365 g (3.72 moles) phosphoric acid were in the reaction mixture. Thus, the remaining water and the maleic acid used constituted a 60 wt % maleic acid solution and the phosphoric acid to maleic acid weight ratio was 3.65. The phosphoric acid/maleic acid molar ratio was 4.33.

The reaction mixture was heated to reflux. After 2 hours at a reflux temperature of 305° F. (151.7° C.) the precipitated fumaric acid product was filtered, washed with water and dried as described in Example 1 above. The fumaric acid yield was about 59%.

EXAMPLE 4

In this Example, 100 g. (0.86 mole) of maleic acid, 92 g. of water and 450 g. of 105% polyphosphoric acid were added to a round-bottom flask as described in Example 1. It was assumed that 27 g. of the water used was needed for hydrolyzing the polyphosphoric acid to 100% orthophosphoric acid, therefore, 477 g phosphoric acid were in the reaction mixture. The remaining water and the maleic acid used constituted a 60 wt % maleic acid solution, and the phosphoric acid to maleic acid ratio weight ratio was 4.77. The phosphoric acid/maleic acid molar ratio was 5.66.

The reaction mixture was heated, and after 2 hours at a reflux temperature of 325° F. (162.8° C.) the fumaric acid precipitate was recovered and treated as in Example 1. The fumaric acid yield was about 80%. Infrared spectroscopy showed the product to be pure fumaric acid with no other detectable components.

EXAMPLE 5

In this Example, 100 g. (0.86 mole) of maleic acid, 95 g. of water and 500 grs of 105% polyphosphoric acid were added to a round-bottom flask as described in Example 1. It was assumed that 30 g. of the water used was needed for hydrolyzing the polyphosphoric acid to 100% orthophosphoric acid, giving 530 g (5.41 moles) of 100% phosphoric acid. Thus the remaining water and the maleic acid used constituted a 60 wt % maleic acid solution and the phosphoric acid to maleic acid weight ratio was 5.3. The phosphoric acid/maleic acid molar ratio was 6.29.

The reaction mixture was heated and, after 3 hours at a reflux temperature of 326° F. (163.3° C.) the fumaric acid precipitate was recovered and treated as in Example 1. The fumaric acid yield was about 83%. Infrared spectroscopy of the product showed it to be pure fumaric acid with no other detectable components.

EXAMPLE 6

This Example was carried out at a maleic acid concentration similar to that of Example 1. The phosphoric acid to maleic acid weight ratio was significantly higher at 4.24. Thus, 100 g. of maleic acid (0.86 mole), 400 g. of 105% polyphosphoric acid, and 222 g. of distilled and deionized water were added to a 2-liter round bottom flask. The round bottom flask was fitted with a Dean Stark trap for water collection. Assuming that 24 g. of water were needed for the polyphosphoric acid hydrolysis, the initial maleic acid concentration was about 25 wt %, and the amount of 100% phosphoric acid was 424 g (4.33 moles). The phosphoric acid to maleic acid weight ratio was 4.24. The phosphoric acid/maleic acid molar ratio was 5.03.

The reflux temperature started out at 257° F. (125° C.). To increase the reflux temperature water was stripped off in 20 ml aliquots every 5 minutes. During the total 1.5 hour reaction time the reflux temperature increased about 9° F. (about 5° C.) for every 20 ml of water removed. At the end of the reaction the temperature was 319–322° F. (159.4–151.1° C.). The fumaric acid formed was filtered, washed with water and dried in vacuum at 200° F. (93.3° C.) for 16 hours. The fumaric acid yield was 55%.

EXAMPLE 7

In this Example 100 g. (0.86 mole) of maleic acid were added to 300 g. of 105% polyphosphoric acid and 16.7 g. of water. Since no additional water to the water needed for hydrolyzing the polyphosphoric acid was used the maleic acid concentration was 100 wt %. Assuming the 16.7 g of water were needed to hydrolyze the polyphosphoric acid to 100% orthophosphoric acid, the amount of 100% orthophosphoric acid in the reaction mixture was 316.7 g (3.23 moles) As expected no reflux was observed and hence the temperature was controlled by controlling the heat input. In one hour of reaction where the temperature was controlled between 318° F. to 331° F. (158.9–166.1° C.), solid precipitation was observed, but the reaction solution was turning dark orange brown and vapors were observed in the vapor space of the flask and the condenser indicating that decomposition may be occurring. The reaction was not continued further. Fumaric acid precipitate was recovered and treated as in Example 1. The fumaric acid yield was about 37%.

The following examples show that fumaric acid can be formed in high yield at significantly lower phosphoric acid to maleic acid weight ratios than those for Examples 2–6.

EXAMPLE 8

In this Example the maleic acid concentration in water was similar to Examples 2–6 but the phosphoric acid to maleic acid ratio was 1.3. The reaction mixture comprised 200 g. (1.72 moles) maleic acid, 244 g. 105% polyphosphoric acid and 143 g. of water which were added to a round bottom flask as in Example 1. 15 g. of the water used were considered to be the hydrolysis water needed to convert 244 g. of 105% polyphosphoric acid to about 259 g (2.64 moles) 100% orthophosphoric acid. Thus the maleic acid concentration was about 61 wt % and the phosphoric acid to maleic acid weight ratio was 1.3. The phosphoric acid/maleic acid molar ratio was 1.53.

During reflux which started at 258° F. (125.6° C.), water was stripped off by use of a Dean-Stark trap which was connected to the condenser at the side of the round bottom flask during equipment setup. Throughout the 5 hour reflux about 81 grs of water were stripped in the first two hours bringing the maleic acid concentration to about 81 wt % and the reflux temperature to 318° F. (158.9° C.). Fumaric acid precipitate was recovered and treated as in Example 1. The fumaric acid yield was about 86%.

EXAMPLE 9

This Example was similar to Example 8 except that 99 g. of water was stripped from the reaction mixture after about 5 hours of reflux bringing the maleic acid concentration to about 87 wt %. The amounts of reagents were: 200 g. maleic acid (1.72 moles), 244 g. 105% polyphosphoric acid and 143 g. of water. Recall that 15 g. of the water used are considered the hydrolysis water needed to convert 244 g. of 105% polyphosphoric acid to about 259 g (2.64 moles) 100% orthophosphoric acid. Thus the maleic acid concentration in water was about 61 wt % and the phosphoric acid to maleic acid weight ratio was 1.3. The phosphoric acid/maleic acid molar ratio was 1.53 The reaction mixture was refluxed for 5 hours at a temperature of about 259° F. (126.1° C.). The reaction mixture was refluxed for an additional 2.5 hours during which 99 g. of water were stripped from the reaction mixture and the reflux temperature lined-out in the 327–331° F. (163.9–166.1° C.) range. Fumaric acid precipitate was recovered and treated as in Example 1. The fumaric acid yield was about 88%.

EXAMPLE 10

In this Example 300 g. of maleic acid (2.58 moles), 68 g. of water and 300 g. of 105% polyphosphoric acid were used in the reaction mixture. Thus the maleic acid concentration was 86 wt %, and the phosphoric acid to maleic acid weight ratio was 1.06. Recall that 18 g. of the water used is assumed to be needed for hydrolysis of the 105% polyphosphoric acid to give 318 g (3.24 moles) of 100% orthophosphoric acid. The phosphoric acid/maleic acid molar ratio was 1.26. The reaction mixture was heated to reflux. During three hours of reaction the reflux temperature increased from 308 to 322° F. (153.3–161.1° C.). The fumaric acid formed was isolated by filtration, washed with water and dried in a vacuum oven. The yield of fumaric acid was about 90%.

EXAMPLE 11

To demonstrate mother liquor recyclability of this process, 654 grs of mother liquor from Example 10 which contained about 250 grs of wash water was used in a reaction with 300 grs (2.58 moles) of maleic acid. The phosphoric acid/maleic acid weight ratio and the phosphoric acid/maleic acid molar ratio were the same as for Example 10. During three hours of reflux about 248 grs of water were stripped and the temperature increased gradually from 244° F. to 333° F. (117.8° C. to 167.2° C.). The fumaric acid formed was isolated by filtration, washed with water and dried in a vacuum oven. The fumaric acid yield was about 103%. This above 100% yield indicated that the fumaric acid which was in the mother liquor was recovered.

EXAMPLE 12

This Example was similar to Example 10 except reagent grade 85% phosphoric acid was used. Thus 300 grs of maleic acid (3.58 moles) and 345 grs of 85% phosphoric acid (293 g; 3.24 moles phosphoric acid) were reacted for 5 hours at a reflux temperature of 325–327° F. (162.8–163.9° C.). Based on the water content of the 85% phosphoric acid, the maleic acid concentration was about 86 wt % and the phosphoric acid to maleic acid weight ratio was about 0.98. The phosphoric acid/maleic acid molar ratio was 1.16. The fumaric acid formed was isolated by filtration, washed with water and dried in a vacuum oven. The fumaric acid yield was about 90%.

EXAMPLE 13

Maleic acid (400.08 g.; 3.45 moles) and phosphoric acid [345.13 g of an 85% aqueous solution of phosphoric acid which is equal to 293 g (2.99 moles) of 100% orthophosphoric acid] were placed in a 3-neck round bottom flask with a reflux attachment. Based on the water content of the 85% phosphoric acid, the maleic acid concentration was about 88.5 wt % and the phosphoric acid to maleic acid weight ratio was about 0.73. The phosphoric acid/maleic acid molar ratio was 0.87. The reaction mixture was heated to reflux with stirring. The reaction mixture was refluxed at a temperature of 315° F. to 340° F. (157.2–171.1° C.) over a period of about 3 hours. The reaction mixture was cooled and about 250 ml of distilled, deionized water was added to form a slurry of water and fumaric acid. The slurry was filtered to recover the fumaric acid solids. The recovered solids were allowed to dry for about 10 minutes and then a second 250 ml water wash was added with mixing for about 2 minutes to form a slurry. The water was removed by filtration and the recovered fumaric acid solids were dried for about 4 hours to give about 368 g fumaric acid, which is a yield of 92%.

That which is claimed is:

1. A process for producing fumaric acid which comprises heating a reaction mixture consisting essentially of maleic acid, phosphoric acid, and water to reflux in an open system at atmospheric pressure and at a temperature of at least about 290° F. to convert the maleic acid to fumaric acid, and recovering the fumaric acid.

2. A process for producing fumaric acid which comprises heating a reaction mixture consisting essentially of maleic acid, phosphoric acid, and water to reflux in an open system at atmospheric pressure and at a temperature of about 290° F. to about 360° F. to convert the maleic acid to fumaric acid; recovering the fumaric acid, and, optionally, washing the recovered fumaric acid with water to remove impurities and obtain pure fumaric acid.

3. The process of claim 2 wherein the reaction mixture is heated to a temperature of about 290° F. to about 350° F.

4. The process of claim 3 wherein the reaction mixture is heated to a temperature of about 290° F. to about 340° F.

5. The process of claim 4 wherein the reaction mixture is heated to a temperature of about 310° F. to about 340° F.

6. The process of claim 1 wherein the mole ratio of phosphoric acid to maleic acid is from about 0.5:1 to about 24:1.

7. The process of claim 6 wherein the mole ratio of phosphoric acid to maleic acid is from about 0.5:1 to about 6:1.

8. The process of claim 7 wherein the mole ratio of phosphoric acid to maleic acid is from about 1:1 to about 6:1.

9. A process for producing fumaric acid which comprises heating a reaction mixture consisting essentially of maleic acid, phosphoric acid, and water, wherein the mole ratio of phosphoric acid to maleic acid is from about 0.5:1 to about 24:1, to a temperature of about 290° F. to about 360° F. in an open system at atmospheric pressure to convert the maleic acid to fumaric acid; recovering the fumaric acid, and, optionally, washing the recovered fumaric acid with water to remove impurities and obtain pure fumaric acid.

10. The process of claim 9 wherein the mole ratio of phosphoric acid to maleic acid is from about 0.5:1 to about 6:1, and wherein the reaction mixture is heated to a temperature of about 290° F. to about 350° F.

11. The process of claim 9 wherein the mole ratio of phosphoric acid to maleic acid is from about 0.5:1 to about 6:1, and wherein the reaction mixture is heated to a temperature of about 290° F. to about 340° F.

12. The process of claim 9 wherein the mole ratio of phosphoric acid to maleic acid is from about 1:1 to about 6:1, and wherein the reaction mixture is heated to a temperature of about 310° F. to about 340° F.

13. The process of claim 9 wherein the mole ratio of water to maleic acid is from about 0.1:1 to about 16:1 and the reaction mixture is heated to a temperature of about 290° F. to about 340° F.

14. The process of claim 9 wherein the mole ratio of water to maleic acid is from about 0.5:1 to about 16:1.

15. The process of claim 9 wherein the mole ratio of water to maleic acid is from about 0.5:1 to about 4:1.

16. The process of claim 9 wherein the mole ratio of water to maleic acid is from about 1:1 to about 4:1.

17. A process according to claim 9 for producing fumaric acid which comprises heating a reaction mixture consisting essentially of maleic acid, phosphoric acid, and water, wherein the mole ratio of phosphoric acid to maleic acid is from about 0.5:1 to about 24:1, and the mole ratio of water to maleic acid is from about 0.1:1 to about 16:1, to a temperature of about 290° F. to about 360° F. in an open system at atmospheric pressure to convert the maleic acid to fumaric acid; recovering the fumaric acid, and, optionally, washing the recovered fumaric acid with water to remove impurities and obtain pure fumaric acid.

18. The process of claim 17 wherein the mole ratio of phosphoric acid to maleic acid is from about 0.5:1 to about 6:1, and the mole ratio of water to maleic acid is from about 0.5:1 to about 16:1, and wherein the reaction mixture is heated to a temperature of about 290° F. to about 350° F.

19. The process of claim 17 wherein the mole ratio of phosphoric acid to maleic acid is from about 0.5:1 to about 6:1, and the mole ratio of water to maleic acid is from about 0.5:1 to about 16:1, and wherein the reaction mixture is heated to a temperature of about 290° F. to about 340° F.

20. The process of claim 17 wherein the mole ratio of phosphoric acid to maleic acid is from about 0.5:1 to about 6:1, and the mole ratio of water to maleic acid is from about 0.5:1 to about 16:1, and wherein the reaction mixture is heated to a temperature of about 290° F. to about 340° F.

21. The process of claim 17 wherein the mole ratio of phosphoric acid to maleic acid is from about 1:1 to about 6:1, and the mole ratio of water to maleic acid is from about 1:1 to about 16:1, and wherein the reaction mixture is heated to a temperature of about 290° F. to about 340° F.

22. The process of claim 19 wherein the mole ratio of phosphoric acid to maleic acid is from about 1:1 to about 6:1, and the mole ratio of water to maleic acid is from about 1:1 to about 4:1, and wherein the reaction mixture is heated to a temperature of about 290° F. to about 340° F.

23. The process of claim 19 wherein the mole ratio of phosphoric acid to maleic acid is from about 1:1 to about 6:1, and the mole ratio of water to maleic acid is from about 1:1 to about 4:1, and wherein the reaction mixture is heated to a temperature of about 310° F. to about 340° F.

* * * * *

UNITED STATES PATENT AND TRADEMARK OFFICE
CERTIFICATE OF CORRECTION

PATENT NO. : 6,103,935
DATED : August 15, 2000
INVENTOR(S) : Muin S. Haddad

It is certified that error appears in the above-identified patent and that said Letters Patent is hereby corrected as shown below:

Column 1,
Line 12, "Fumaric acid us used" should read -- Fumaric acid is used --
Line 26, "with acceptable, odor, color," should read -- with acceptable odor, color, --

Column 3,
Line 44, "hydrocarbon by-products and" should read -- hydrocarbon by products and --

Column 4,
Line 7, "process the present invention" should read -- process of the present invention --

Column 8,
Line 47, "316.7g (3.23 moles)" should read -- 316.7g. (3.23 moles). --

Column 9,
Line 2, "Example 1. 15 g. of the" should read -- Example 1.15 g. of the --
Line 31, "1.53 The reaction mixture" should read -- 1.53. The reaction mixture --

Signed and Sealed this

Twenty-seventh Day of July, 2004

JON W. DUDAS
*Acting Director of the United States Patent and Trademark Office*